(12) United States Patent
Lei et al.

(10) Patent No.: US 11,311,467 B2
(45) Date of Patent: *Apr. 26, 2022

(54) POLYUREA CAPSULES PREPARED WITH A POLYISOCYANATE AND CROSS-LINKING AGENT

(71) Applicant: International Flavors & Fragrances Inc., New York, NY (US)

(72) Inventors: Yabin Lei, Holmdel, NJ (US); Li Xu, Newark, NJ (US); Carol Joyce, Toms River, NJ (US); Lewis Michael Popplewell, Morganville, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 229 days.

This patent is subject to a terminal disclaimer.

(21) Appl. No.: 13/967,800

(22) Filed: Aug. 15, 2013

(65) Prior Publication Data

US 2013/0330292 A1 Dec. 12, 2013

Related U.S. Application Data

(63) Continuation-in-part of application No. 13/163,320, filed on Jun. 17, 2011, which is a continuation-in-part of application No. 12/883,337, filed on Sep. 16, 2010, now abandoned, which is a continuation-in-part of application No. 12/562,578, filed on Sep. 18, 2009, now Pat. No. 8,299,011.

(51) Int. Cl.

| | |
|---|---|
| *A61K 8/11* | (2006.01) |
| *A61K 8/04* | (2006.01) |
| *A61Q 5/00* | (2006.01) |
| *A61Q 5/12* | (2006.01) |
| *C11D 3/50* | (2006.01) |
| *B01J 13/20* | (2006.01) |
| *A61K 8/73* | (2006.01) |
| *A61K 8/84* | (2006.01) |
| *B01J 13/14* | (2006.01) |
| *B01J 13/16* | (2006.01) |
| *C11D 17/00* | (2006.01) |
| *A61Q 5/02* | (2006.01) |
| *A61Q 13/00* | (2006.01) |
| *C11B 9/00* | (2006.01) |

(52) U.S. Cl.
CPC .................. *A61K 8/11* (2013.01); *A61K 8/04* (2013.01); *A61K 8/731* (2013.01); *A61K 8/84* (2013.01); *A61Q 5/00* (2013.01); *A61Q 5/02* (2013.01); *A61Q 5/12* (2013.01); *A61Q 13/00* (2013.01); *B01J 13/14* (2013.01); *B01J 13/16* (2013.01); *B01J 13/206* (2013.01); *C11B 9/00* (2013.01); *C11D 3/505* (2013.01); *C11D 17/0039* (2013.01); *A61K 2800/412* (2013.01); *A61K 2800/624* (2013.01); *A61K 2800/805* (2013.01)

(58) Field of Classification Search
CPC . A61K 8/11; A61K 8/04; A61K 8/731; A61K 8/84; A61K 2800/412; A61K 2800/624; A61K 2800/805; A61Q 5/12; A61Q 5/00; A61Q 5/02; A61Q 13/00; B01J 13/14; B01J 13/16; B01J 13/206; C11D 3/505; C11D 17/0039; C11B 9/00
See application file for complete search history.

(56) References Cited

U.S. PATENT DOCUMENTS

| | | | |
|---|---|---|---|
| 3,743,601 A | | 7/1973 | Schnoring et al. |
| 3,963,680 A | * | 6/1976 | O'Keefe et al. ............... 528/53 |
| 4,021,595 A | * | 5/1977 | Kiritani ................... B01J 13/16 503/213 |
| 4,280,833 A | | 7/1981 | Beestman et al. ............ 504/300 |
| 4,563,212 A | | 1/1986 | Becher et al. |
| 4,608,227 A | | 8/1986 | Preiss |
| 4,640,709 A | | 2/1987 | Beestman ...................... 504/300 |
| 4,650,769 A | * | 3/1987 | Kakimi .................. B01J 13/16 428/402.2 |
| 4,785,048 A | | 11/1988 | Chao et al. |
| 4,798,862 A | | 1/1989 | Gillis .......................... 524/783 |
| 5,164,126 A | * | 11/1992 | Kalishek et al. ........ 428/402.21 |
| 5,304,448 A | | 4/1994 | Keoshkerian et al. |
| 5,324,584 A | * | 6/1994 | Juang et al. ................. 264/4.7 |
| 5,635,211 A | | 6/1997 | Nehen et al. ................. 424/489 |
| 5,705,174 A | * | 1/1998 | Benoff ..................... B01J 13/16 264/4.1 |
| 5,866,153 A | | 2/1999 | Hasslin et al. |
| 5,925,595 A | * | 7/1999 | Seitz .................. C08G 18/7831 504/359 |

(Continued)

FOREIGN PATENT DOCUMENTS

| | | |
|---|---|---|
| EP | 1693104 A1 | 8/2006 |
| JP | 5068970 A | 6/1975 |

(Continued)

OTHER PUBLICATIONS

Office Communication dated Oct. 18, 2011 from U.S. Appl. No. 12/562,578, filed Sep. 18, 2009.

(Continued)

*Primary Examiner* — Doan T Phan
(74) *Attorney, Agent, or Firm* — Licata & Tyrrell P.C.

(57) ABSTRACT

Polyurea capsules that encapsulate active materials in polymeric walls resulting from the polymerization of an aromatic or aliphatic polyisocyanate and a cross-linking agent are provided as are consumer products containing said polyurea capsules and for methods for producing such capsules.

1 Claim, 2 Drawing Sheets

(56) References Cited

U.S. PATENT DOCUMENTS

| | | | |
|---|---|---|---|
| 6,133,197 A | 10/2000 | Chen et al. | 504/359 |
| 6,340,653 B1 | 1/2002 | Scher et al. | |
| 6,586,107 B2 | 7/2003 | Klug et al. | 503/215 |
| 6,797,670 B2 | 9/2004 | Kleban et al. | 503/215 |
| 7,125,835 B2 | 10/2006 | Bennett et al. | |
| 7,632,789 B2 | 12/2009 | Brain et al. | |
| 8,026,206 B2 | 9/2011 | Sajic et al. | |
| 8,299,011 B2 | 10/2012 | Lei et al. | 510/438 |
| 2002/0079599 A1 | 6/2002 | Kleban et al. | 264/4.1 |
| 2004/0121155 A1* | 6/2004 | Matsunami et al. | 428/402 |
| 2004/0156742 A1 | 8/2004 | Milan et al. | |
| 2005/0153839 A1* | 7/2005 | Tamura | B41M 5/30 503/215 |
| 2005/0161843 A1* | 7/2005 | Wang | G03F 7/002 264/4.1 |
| 2005/0271735 A1* | 12/2005 | Stover | A01N 25/28 424/490 |
| 2007/0042182 A1* | 2/2007 | Markus et al. | 428/402.2 |
| 2007/0138672 A1 | 6/2007 | Lee et al. | |
| 2007/0202063 A1 | 8/2007 | Dihora et al. | |
| 2008/0103265 A1 | 5/2008 | Schocker et al. | |
| 2008/0131695 A1 | 6/2008 | Aouad et al. | 428/338 |
| 2008/0187596 A1 | 8/2008 | Dihora et al. | |
| 2008/0200363 A1 | 8/2008 | Smets et al. | 510/475 |
| 2008/0206291 A1 | 8/2008 | Ouali et al. | 424/401 |
| 2009/0053161 A1 | 2/2009 | Nguyen et al. | 424/70.17 |
| 2010/0009893 A1 | 1/2010 | Cavin et al. | |
| 2010/0086575 A1 | 4/2010 | Dihora et al. | |
| 2010/0119679 A1* | 5/2010 | Dihora | C11D 17/0039 426/534 |
| 2011/0077188 A1 | 3/2011 | Ouali et al. | 512/2 |
| 2011/0077375 A1 | 3/2011 | Kulke | |
| 2011/0230390 A1 | 3/2011 | Ouali et al. | |
| 2012/0016139 A1 | 1/2012 | Screen et al. | |
| 2012/0148644 A1 | 6/2012 | Popplewell et al. | |
| 2013/0109569 A1 | 5/2013 | Dave et al. | |
| 2013/0330292 A1 | 12/2013 | Lei et al. | |
| 2013/0337023 A1 | 12/2013 | Lei et al. | |
| 2014/0017287 A1 | 1/2014 | Lei et al. | |
| 2014/0066357 A1* | 3/2014 | Yao | B01J 13/16 512/2 |

FOREIGN PATENT DOCUMENTS

| | | | | |
|---|---|---|---|---|
| WO | WO 2004/098767 | | 11/2004 | |
| WO | WO 2006/006003 | | 1/2006 | |
| WO | 20071347441 A1 | | 12/2007 | |
| WO | WO 2008031241 A1 * | | 3/2008 | |
| WO | 2009091726 A1 | | 7/2009 | |
| WO | 2009103615 A1 | | 8/2009 | |
| WO | 2011154893 A1 | | 12/2011 | |
| WO | WO 2011/154893 | | 12/2011 | |
| WO | WO-2011154893 A1 * | | 12/2011 | B01J 13/16 |
| WO | WO-2011161265 A2 * | | 12/2011 | A61K 8/11 |
| WO | 2012107323 A1 | | 8/2012 | |
| WO | WO 2012/107323 | | 8/2012 | |
| WO | 2013000587 A1 | | 1/2013 | |
| WO | WO 2013/000587 | | 1/2013 | |
| WO | 2013059167 A2 | | 4/2013 | |
| WO | 2013092958 A1 | | 6/2013 | |

OTHER PUBLICATIONS

Office Communication dated Aug. 21, 2012 from U.S. Appl. No. 13/163,320, filed Jun. 17, 2011.
Office Communication dated Nov. 21, 2012 from U.S. Appl. No. 13/163,320, filed Jun. 17, 2011.
EP Extended Search Report dated Mar. 31, 2017 from 14836347.9 filed Aug. 15, 2014.
Dow Plastics—"PAPI 135". Retrieved on Jan. 3, 2017. Retrieved from the internet <URL: http://msdssearch.dow.com/PublishedliteratureDOWCOM/dh_003f/0901b8038003f163.pdf>.
Chinese First Office Action dated Jan. 30, 2014 for Application No. CN 201010548980.0(with English Translation included).

* cited by examiner

POLYUREA CAPSULES PREPARED WITH A POLYISOCYANATE AND CROSS-LINKING AGENT

This application is a continuation-in-part of U.S. patent application Ser. No. 13/163,320, filed Jun. 17, 2011, which is a continuation-in-part of U.S. patent application Ser. No. 12/883,337, filed on Sep. 16, 2010, now abandoned, which is a continuation-in-part of U.S. patent application Ser. No. 12/562,578, filed on Sep. 18, 2009, now U.S. Pat. No. 8,299,011, the contents of which are incorporated herein by reference in their entirety.

BACKGROUND

Microencapsulation is used in a variety of different applications where a compound needs to be delivered or applied to a target area, protected from its environment, or released in a time-delayed way or only after a treatment has been applied that triggers release. Various techniques for preparing microcapsules are known in the art and are used, depending on the contents to be encapsulated, the environment in which the microcapsules should retain their integrity and the desired release mechanism.

Interfacial polycondensation is a known technique for preparing microcapsules and versatile microcapsule wall materials are used including polyureas and polyurethanes (WO 2011/154893, WO 2012/107323, US 2011/0077188, U.S. Pat. No. 5,635,211, U.S. Pat. No. 6,586,107, and U.S. Pat. No. 6,797,670). Such wall materials are produced by having a first phase which is water-immiscible and includes a polyfunctional isocyanate, i.e., a diisocyanate and/or a polyisocyanate, and a second aqueous phase that may include a polyfunctional alcohol or amine, i.e., a diol and/or polyol, for obtaining a polyurethane capsule wall or a diamine and/or polyamine having —NH$_2$ and/or —NH groups.

If the active material to be encapsulated is hydrophobic, it will be included in the water-immiscible phase, thereafter the two phases are mixed by high shear mixing to form an oil-in-water emulsion. In this emulsion, the polycondensation reaction will take place. Thus, the small droplets of the water-immiscible phase will be surrounded by the microcapsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form microcapsule walls surrounding the droplets of water-miscible phase. Suitable emulsifiers are often utilized to aid in the preparation and stabilization of the emulsion.

Suitable raw materials and processes for preparing microcapsules by polycondensation are described in U.S. Pat. No. 4,640,709 and the literature described therein. As is exemplified therein, and also in U.S. Pat. No. 6,133,197, polyurea and polyurethane microcapsules are often used for rugged applications, such as for encapsulation of agrochemicals, e.g., herbicides and pesticides, where slow time-release is desired to set the agents free. For such applications, the microcapsules also require a relatively high mechanical strength. For the polycondensation reaction, suitable diisocyanate and symmetrical triisocyanate starting materials are disclosed in the prior art.

WO 2011/154893 discloses a process for the preparation of capsules, which includes mixing at least one aliphatic polyisocyanate and of at least one aromatic polyisocyanate, wherein the molar ratio between the two polyisocyanates is between 75:25 and 20:80.

WO 2013/000587 discloses a process for the preparation of polyurea microcapsules, which includes dissolving at least one polyisocyanate having at least two isocyanate functional groups, in a perfume to form a solution; adding to the solution an aqueous solution of an emulsifier or of a colloidal stabilizer; and adding to the mixture to 3,5-di-amino-1,2,4-triazole to form a polyurea wall.

Polyurea or polyurethane microcapsules have thus far not be applied for the release of benefit agents intended for laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is a method for preparing a polyurea capsule composition by preparing an oil phase comprising an active material and a polyisocyanate; preparing a surfactant solution; emulsifying the oil phase into the surfactant solution to form a fragrance emulsion; adding a cross-linking agent to the fragrance emulsion to form a capsule slurry; and curing the capsule slurry. In one embodiment, the active material is a fragrance oil. In some embodiments, the polyisocyanate is an aromatic polyisocyanate containing a phenyl, a toluoyl, a xylyl, a naphthyl or a diphenyl moiety (e.g., a polyisocyanurate of toluene diisocyanate, a trimethylol propane-adduct of toluene diisocyanate or a trimethylol propane-adduct of xylylene diisocyanate), an aliphatic polyisocyanate (e.g., a trimer of hexamethylene diisocyanate, a trimer of isophorone diisocyanate and a biuret of hexamethylene diisocyanate), or a mixture thereof (e.g., a mixture of a biuret of hexamethylene diisocyanate and a trimethylol propane-adduct of xylylene diisocyanate). In other embodiments, the surfactant is polyvinyl alcohol, polystyrene sulfonate, carboxymethyl cellulose, sodium salt of naphthalene sulfonate condensate, or a mixture thereof. In still other embodiments, the cross-linking agent is a polyamine (e.g., diethylenetriamine, bis(3-aminopropyl) amine, bis(hexanethylene)triamine, tris(2-aminoethyl) amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate). In certain embodiments, the step of adding the cross-linking agent to the fragrance emulsion is at a temperature of 35° C. or 22° C. In particular embodiments, the capsule slurry is cured at a temperature greater than about 55° C., 65° C., 75° C., 85° C. or 95° C. In a further embodiment, the method further includes the steps of adding a salt to the cured capsule slurry and washing the capsule slurry with water.

A polyurea capsule composition, optionally containing a deposition aide, and consumer product containing said polyurea capsule composition are also provided, wherein the consumer product can be in the form of a shampoo, a hair conditioner, a soap, a body wash or other hygiene product, a cosmetic preparation, a body liquid detergent, an all-purpose cleaner, a fabric softener or refresher, an ironing water or a detergent, softener or drier sheet.

DETAILED DESCRIPTION OF THE INVENTION

It has been found that polyurea microcapsules prepared with a polyisocyanate and amine are very suitable for carrying various kinds of hydrophobic or hydrophilic benefit agents of use in products intended for application to animate and inanimate surfaces. Therefore, the present invention is a microcapsule composition and related process, wherein said microcapsule is composed of an encapsulating polymer and an active material encapsulated by the encapsulating polymer, wherein the encapsulating polymer is the reaction product of polymerization between a polyisocyanate and at least one amine. Microcapsules of this invention are of particular use in personal care including shampoo, conditioner, personal wash, personal cleaners and sanitizers, fabric care such as fabric refresh, industrial cleaners, liquid and powder detergent and rinse conditioners.

Polyisocyanate.

The polyurea microcapsules of this invention are prepared using a polyisocyanate with the general structure O=C=N—R—N=C=O, wherein said polyisocyanate can be aromatic, aliphatic, linear, branched, or cyclic. In certain embodiments, the polyisocyanate preferably contains, on average, 2 to 4 —N=C=O groups. In particular embodiments, the polyisocyanate contains at least three isocyanate functional groups. In certain embodiments, the polyisocyanate is water insoluble.

In particular embodiments, the polyisocyanate of the invention is an aromatic polyisocyanate. Desirably the aromatic polyisocyanate includes a phenyl, a toluoyl, a xylyl, a naphthyl or a diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

In yet other embodiments, the polyisocyanate is an aliphatic polyisocyanate. In certain embodiments, the aliphatic polyisocyanate is a trimer of hexamethylene diisocyanate, a trimer of isophorone diisocyanate or a biuret of hexamethylene diisocyanate.

In particular embodiments, the polyisocyanate of the invention has the structure:

or its structural isomer. Representative polyisocyanates having this structure are commercially available and include, but are not limited to TAKENATE D-110N (Mitsui), DESMODUR L75 (Bayer), and DESMODUR IL (Bayer).

TAKENATE D-110N

DESMODUR L75

DESMODUR IL

In some embodiments of this invention, the polyisocyanate used in the preparation of the polyurea capsules of this invention is a single polyisocyanate. In other embodiments the polyisocyanate used in the preparation of the polyurea capsules of this invention is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate.

The range of polyisocyanate concentration in the polyurea capsule composition can vary from 10% to 0.1%, and is preferable from 5% to 0.25%.

Cross Linking Agent.

In another embodiment of the invention, the encapsulating wall material of the microcapsule contains one or more amines as cross-linking agents. In particular embodiments of this invention, the amine is a polyamine. Water soluble polyamines or polyamine salts are preferred as the amine is typically present in the aqueous phase. Two classes of such amines include polyalkylene polyamines having the following structures:

$$H-(NH(CH_2)_m)_n-NH_2$$

$$H_2N(CH_2)x-\underset{H}{\overset{R}{C}}-N(CH_2)y-\underset{H}{\overset{R}{C}}-NH_2$$
$$|$$
$$(CH_2)z$$
$$|$$
$$HC-R$$
$$|$$
$$NH_2$$

where R is hydrogen or —$CH_3$; and m, n, x, y, and z are 1, 2, 3, 4, and 5, respectively, e.g., diethylene triamine, triethylene tetramine, and the like.

Specific examples of cross-linking agents of use in this invention, include the following:

$H_2N\diagdown\diagup N_H\diagdown\diagup NH_2$
Diethylenetriamine $H_2N\diagdown\diagdown\diagup N_H\diagdown\diagdown\diagup NH_2$
Bis (3-aminopropyl) amine Tris (2-aminoethyl) amine $H_2N\diagdown\diagdown\diagdown\diagdown\diagdown\diagup N_H\diagdown\diagdown\diagdown\diagdown\diagdown NH_2$
Bis (hexanethylene) triamine $H(NHCH_2CH_2)_5NH_2$
Pentaethylenehexamine $H_2N\diagdown\diagup N_H\diagdown\diagup N_H\diagdown\diagup NH_2$
Triethylenetetramine 1,3-Diaminoguanidine monohydrochloride

N, N'-Bis (3-aminopropyl)-1, 3-propanediamine 1,1-Dimethylbiguanide hydrochloride Tetraethylenepentamine Guanidine carbonate Branched Polyethylenimine Chitosan Nisin Gelatin The range of polyamine concentration or the total amine concentration in the polyurea capsule composition can vary from 5% to 0.1%, and is preferably in the range of 2% to 0.25%.

In one embodiment of the invention, the cross linking agent is added to the microcapsule reaction at a temperature of 35° C. In another embodiment, the cross linking agent is added to the microcapsule reaction at a temperature of 22° C.

Capsule Formation Aid.

In another embodiment of the invention, a microcapsule composition is provided that contains an active material that is encapsulated by a polyurea polymer which are reacted in the presence of a capsule formation aid, e.g., a surfactant or dispersant. For the purpose of this invention, capsule formation aids improve the performance of the microcapsule system. Performance is measured by the intensity of the fragrance release during the pre-rub phase and post-rub. The pre-rub phase is the phase when the microcapsules have been deposited on the cloth, e.g., after a fabric softener containing microcapsules has been used during the wash cycle. The post-rub phase is after the microcapsules have been deposited and the capsules are broken by friction or other similar mechanisms.

In some embodiments, the capsule formation aid is a surfactant such as polyvinyl alcohol (PVA), polystyrene sulfonate (PSS), carboxymethyl cellulose (CMC), sodium salt of naphthalene sulfonate condensate, or a mixture thereof. In general, the range of surfactant concentration in the microcapsule composition varies from 5% to 0.1% and preferable from 2% to 0.25%.

Commercially available surfactants include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Core/Active Materials.

The core of the microcapsules of the invention can include one or more active materials including, but not limited to, flavors and/or fragrance ingredients such as fragrance oils. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butyl-cyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1- yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for, example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-4,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha,alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl)propanal, 3-(4-tert.-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methyl-N-methylanthranilate, Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemongrass oil, lovage oil, lime oil distilled, lime oil expressed, linaloe oil, *Litsea cubeba* oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total capsule suspension, preferably from about 60% to about 10% of the total capsule suspension, and most preferably from about 50% to about 20% of the total capsule suspension.

In addition to the fragrance materials, the present invention also contemplates the incorporation of other core additives including solvent, emollients, and core modifier materials encapsulated by the encapsulating polymer.

The present invention also contemplates the incorporation of solvent materials, particles or polymeric core modifiers into the core. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should denoted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO-[OCH_2-CH(OCOR_1)-CH2O-]_n$, where $R_1$ and $R_2$ can be H or $C_{4-26}$ aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIOSOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), magenase (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Deposition Aids.

Deposition aids can also be used to aid in deposition of capsules to surfaces such as fabric, hair or skin. These include but are not limited to anionically, cationically, non-ionically, or zwitterionically charged water-soluble polymers which can be applied to the polyurea capsule. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein, molecular weight is provided as weight average molecular weight.

Particular examples of cationic polymers that can be used to coat the polyurea capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDADMAC on cellulose, e.g., CELQUAT L-200 (POLYQUATERNIUM-4), POLYQUATERNIUM-10 and POLYQUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

wherein, $R_1$ is any alkane from C1-C25 or H, wherein the number of double bonds ranges from 0-5, $R_1$ is an alkoxylated fatty alcohol with any alkoxy carbon-length of C1-C25, or $R_1$ is a liquid crystalline moiety that can provide the polymer with thermotropic liquid crystalline properties $R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

wherein, $R_1$ is any alkane from C1-C25 or H with number of double bonds from 0-5, $R_1$ is an alkoxylated fatty alcohol with a C1-C25 alkyl chain length, or $R_1$ is a liquid crystalline moiety that provides the polymer with thermotropic liquid crystalline properties;

$R_2$ is H or $CH_3$;

$R_3$ is a C1-25 alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. No. 4,395,541 and U.S. Pat. No. 4,597,962;

iii) adipic acid/dimethyl amino hydroxypropyl diethylene triamine copolymers, such as CARTARETIN F-4 and F-23, commercially available from Sandoz;

iv) polymers of the general formula: —[N($CH_3$)$_2$—($CH_2$)$_x$—NH—(CO)—NH—($CH_2$)$_y$—N($CH_3$)$_2$)—($CH_2$)$_z$—O—(—$CH_2$)$_p$]$_n$—, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si($R_1$)($R_2$)—O—]$_x$—[Si($R_3$)($R_2$)—O—]$_y$— where $R_1$ is any alkane from C1-C25 or H with number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be —$R_1$—$R_4$, where $R_4$ can be —$NH_2$, —NHR$_1$, —NR$_1$R$_2$, —NR$_1$R$_2$R$_6$ (where R$_6$=R$_1$, R$_2$, or —CH$_2$—COOH or its salt), —NH—C(O)—, —COOH, —COO— alkali salt, any C1-25 alcohol, —C(O)—NH$_2$ (amide), —C(O)—N(R$_2$)(R$_2$')(R$_2$"), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-R$_5$ or naphthalene-R$_6$ where R$_5$ and R$_6$ are R$_1$, R$_2$, R$_3$, sulfonic acid or its alkali salt or organic counter ion. R$_3$ can also be —(CH$_2$)$_x$—O—CH$_2$—CH(OH)—CH$_2$—N(CH$_3$)$_2$—CH$_2$—COOH and its salts. Any mixture of these R$_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundam.* 25:120-125.

As indicated, the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion.

In accordance with the compositions and methods disclosed herein, the wall polymer level of the polyurea capsules can be from about 15 to about 0.1% of the total capsule suspension, preferably from about 10 to about 1% of the total capsule suspension, or most preferably from about to about 2% of the total capsule suspension.

In a further embodiment of the invention, the amount of encapsulated active material is from about 80 to about 5% of the total capsule suspension, preferably from about 60% to about 10% of the total capsule suspension, or most preferably from about 50 to about 20% of the total capsule suspension.

In one embodiment of the method, the cross-linking agent is a polyamine, wherein the stoichiometry of the polyamine and polyisocyanate can be manipulated to give reduced amounts of polyisocyanate in the prepared capsule slurry. The stoichiometry of the polyamine to isocyanate will vary from 1 to 1, (one amine group per one isocyanate group), preferably from 2 to 1, (two amine groups per one isocyanate group), and most preferably from 4 to 1 (four amine groups per one isocyanate group).

In certain embodiments of the invention, the capsule slurry is cured at a temperature greater than about 55° C.; greater than about 65° C.; greater than about 75° C.; greater than about 85° C.; greater than about 95° C.; greater than about 105° C. or greater than 120° C.

Microcapsules prepared in accordance with this invention preferably have a size in the range of from 0.1 to 100 microns, or preferably from 0.2 to 50 microns depending on the emulsifier and shear rates used.

Applications.

The present invention is well-suited for use in consumer products including, without limitation, personal care products such as such as shampoos, rinses, hair conditioners, creams, body washes, body soap, body liquid detergent, or other hygiene product; cosmetic preparations; all-purpose cleaners; or laundry products such as laundry detergents, fabric softeners or refreshers, an ironing water, fabric bleaches, fabric brighteners and fabric rinse conditioners, e.g., for high efficiency front load washing machines (e.g., those manufactured by Miele, Germany) or drier sheets. Rinse off products may be liquids, solids, pastes, or gels, of any physical form. Also included in the use of the microcapsules are applications where a second active ingredient is included to provide additional benefits for an application. The additional beneficial ingredients include fabric softening ingredients, skin moisturizers, sunscreen, insect repellent and other ingredients as may be helpful in a given application. Also included are the beneficial agents alone, that is without the fragrance.

Capsules having a polyurea capsule wall are very suitable to carry a variety of hydrophobic or hydrophilic benefit agents to be used in products for application to all kinds of surfaces. On the one hand surfaces may be inanimate, such as hard surfaces found in and around the house, e.g., wooden, metal, ceramic, glass and paint surfaces, or soft surfaces such as clothing, carpets, curtains and other textiles. On the other hand, such surfaces may be animate surfaces, more particularly surfaces of a human or animal body, i.e., human or animal skin and hair. For the purposes of this invention animate surfaces do not include plant surfaces.

Products intended for application to a surface are generally intended for washing/cleaning or for caring/protecting or both. Examples are cleaning products for hard surfaces or textiles, caring/protection products like polishes and waxes for delicate surfaces such as wood, car paint and leather, laundry softening agents, anti-soiling agents, water repelling agents, and the like. Examples of products intended for the human skin are bath and shower products and shampoo for skin and hair cleansing, and all kinds of skin and hair care/protection products such as hair conditioners, hand and body lotions and creams, lip care products, deodorants and antiperspirants, make up products and the like.

The dosage of the microcapsules in the rinse off products is from about 0.05 weight percent to 10 weight percent, preferred 0.2 weight percent to about 5 weight percent, and most preferred 0.5 weight percent to about 2 weight percent.

Cleaning and cleansing compositions will include one or more surfactants that may be chosen from anionic, cationic, nonionic, zwitterionic and amphoteric surfactants known in the art. For cleansing composition for skin or hair the surfactants must obviously meet the condition of being suitable for topical application.

The compositions according to the invention may optionally include a variety of components known in the art and adapted to their specific use. Thus, compositions intended for inanimate surfaces may include components such as builders, sequestrants, hydrotropes, organic solvents, pH regulation components such as organic or inorganic acids and/or bases, thickening agents, chlorine or peroxide bleaches, laundry softening agents, scouring agents, biocides, coloring agents, pearlescent, preservatives, perfumes. Compositions intended for application may contain a variety of vehicles suitable for topical application and a variety of benefit agents for skin or hair.

As described herein, the polyurea capsules of the invention are well-suited for use in a variety of well-known household products such as laundry detergent and fabric softeners, liquid dish detergents, automatic dish detergents, bathroom cleaners, bath tissue, tumble dryer sheets, rug deodorizers, candles, floor cleaners, disinfectants, window cleaners; household devices such as paper towels, disposable wipes, room deodorizers; baby care products such as diaper rash cream/balm or baby powder; baby care devices such as diapers, bibs and wipes; health care devices such as dental floss, toothbrushes, tampons and feminine napkins; personal care products such as personal cleansers (e.g., bar soap or body wash), sunscreen (spray or lotion), wax-based deodorant, glycol/soap-type deodorant, lotion, body powder, shaving cream, bath soak, exfoliating scrub; personal care devices such as facial tissues, and cleansing wipes; hair care products such as shampoo (liquid or dry powder), hair conditioner (rinse out or leave-in), hair fixative or style aids, hair bleaches, dyes or colorants; and beauty care products such as fine fragrances, solid perfume, liquid or powder foundation, eye shadow, and lipstick/lip balm.

These products can employ surfactant and emulsifying systems that are well-known. For example, fabric softener systems are described in U.S. Pat. No. 6,335,315, U.S. Pat. No. 5,674,832, U.S. Pat. No. 5,759,990, U.S. Pat. No. 5,877,145, U.S. Pat. No. 5,574,179; U.S. Pat. No. 5,562,849, U.S. Pat. No. 5,545,350, U.S. Pat. No. 5,545,340, U.S. Pat. No. 5,411,671, U.S. Pat. No. 5,403,499, U.S. Pat. No. 5,288,417, U.S. Pat. No. 4,767,547, and U.S. Pat. No. 4,424,134. Liquid dish detergents are described in U.S. Pat. No. 6,069,122 and U.S. Pat. No. 5,990,065; automatic dish detergent products are described in U.S. Pat. No. 6,020,294, U.S. Pat. No. 6,017,871, U.S. Pat. No. 5,968,881, U.S. Pat. No. 5,962,386, U.S. Pat. No. 5,939,373, U.S. Pat. No. 5,914,307, U.S. Pat. No. 5,902,781, U.S. Pat. No. 5,705,464, U.S. Pat. No. 5,703,034, U.S. Pat. No. 5,703,030, U.S. Pat. No. 5,679,630, U.S. Pat. No. 5,597,936, U.S. Pat. No. 5,581,005, U.S. Pat. No. 5,559,261, U.S. Pat. No. 4,515,705, U.S. Pat. No. 5,169,552, and U.S. Pat. No. 4,714,562. Liquid laundry detergents which can use the present invention include those systems described in U.S. Pat. No. 5,929,022, U.S. Pat. No. 5,916,862, U.S. Pat. No. 5,731,278, U.S. Pat. No. 5,565,145, U.S. Pat. No. 5,470,507, U.S. Pat. No. 5,466,802, U.S. Pat. No. 5,460,752, U.S. Pat. No. 5,458,810, U.S. Pat. No. 5,458,809, U.S. Pat. No. 5,288,431, U.S. Pat. No. 5,194,639, U.S. Pat. No. 4,968,451, U.S. Pat. No. 4,597,898, U.S. Pat. No. 4,561,998, U.S. Pat. No. 4,550,862, U.S. Pat. No. 4,537,707, U.S. Pat. No. 4,537,706, U.S. Pat. No. 4,515,705, U.S. Pat. No. 4,446,042, and U.S. Pat. No. 4,318,818. Shampoo and conditioners that can employ the present invention include those described in U.S. Pat. No. 6,162,423, U.S. Pat. No. 5,968,286, U.S. Pat. No. 5,935,561, U.S. Pat. No. 5,932,203, U.S. Pat. No. 5,837,661, U.S. Pat. No. 5,776,443, U.S. Pat. No. 5,756,436, U.S. Pat. No. 5,661,118, U.S. Pat. No. 5,618,523, U.S. Pat. No. 5,275,755, U.S. Pat. No. 5,085,857, U.S. Pat. No. 4,673,568, U.S. Pat. No. 4,387,090 and U.S. Pat. No. 4,705,681. Toothpastes and other oral care products that can employ the present invention include those described in U.S. Pat. No. 6,361,761, U.S. Pat. No. 6,616,915, U.S. Pat. No. 6,696,044, U.S. Pat. No. 6,193,956, U.S. Pat. No. 6,132,702, U.S. Pat. No. 6,004,538, U.S. Pat. No. 5,939,080, U.S. Pat. No. 5,885,554, U.S. Pat. No. 6,149,894, U.S. Pat. No. 5,505,933, U.S. Pat. No. 5,503,823, U.S. Pat. No. 5,472,685, U.S. Pat. No. 5,300,283 and U.S. Pat. No. 6,770,264.

Personal care products, including cosmetic or pharmaceutical preparations can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the "oil-in-water" (O/W) type or water-in-oil-in-water (W/O/W) type.

As used herein stability of the products is measured at room temperature or above over a period of at least a week. More preferably the capsules of the present invention are allowed to be stored at room temperature for more than about two weeks and preferably more than about a month.

Other active materials that can be included the in polyurea capsules of this invention include antimicrobial agents such as thymol, 2-hydroxy-4,2,4-trichlorodiphenylether, triclocarban; organic sunscreen actives such as oxybenzone, octylmethoxy cinnamate, butylmethoxy dibenzoyln ethane, p-aminobenzoic acid and octyl dimethyl-p-aminobenzoic acid; vitamins such as Vitamin A, Vitamin C and Vitamin E or esters thereof; and malodor counteracting ingredients including, but not limited to, an $\alpha,\beta$-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, and zinc undecenylate.

These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. As used herein all percentages are weight percent unless otherwise noted, ppm is understood to stand for parts per million, mL is understood to be milliliter, g is understood to be gram, and mol is understood to be mole. All materials are reported in weight percent unless noted otherwise. As used herein all percentages are understood to be weight percent. The abbreviations PU stand for polyurea and CMC stands for carboxymethyl cellulose.

The invention is described in greater detail by the following non-limiting examples.

Example 1

Preparation of Polyurea Capsules with TAKENATE D-110N

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a 1.0% surfactant solution (160 g) was prepared by dissolving sufficient amount of FLEXAN II (Akzo Nobel, Bridgewater, N.J.) in deionized (DI) water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules.

The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsule was immediately visible by optical microscopy. The mixer speed was reduced after the addition of tris(2-aminoethyl)amine was complete. The capsule slurry was cured at 55° C. for two hours.

Example 2

Polyurea Capsules Cured at Elevated Temperature

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a 1.0% surfactant solution (160 g) was prepared by dissolving sufficient amount of FLEXAN II (Akzo Nobel, Bridgewater, N.J.) in DI water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules.

The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The temperature was raised to 55° C. and kept at 55° C. for 2 hours and elevated to 75° C. for 2 hours.

Example 3

Polyurea Capsules Prepared with a Blend of Dispersants

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The capsule slurry was cured at 55° C. for two hours.

Example 4

Preparation of Polyurea Capsules with DESMODUR L75

Polyurea capsules were prepared with DESMODUR L75 by carrying out the process described in Example 1 and replacing TAKENATE D-110N with DESMODUR L75.

Example 5

Polyurea Capsule with Elevated Amounts of Isocyanate Precursors and Amine Crosslinkers Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 14.4 g of isocyanate monomer, TAKENATE D-110N (Mitsui Chemicals Corporation, Rye Brook, N.Y.), to form the oil phase. In a separate beaker, a 1.0% surfactant solution (150 g) was prepared by dissolving sufficient amount of FLEXAN II (Akzo Nobel, Bridgewater, N.J.) in DI water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules.

The fragrance emulsion was placed in a round bottom vessel and 15.6 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The capsule slurry was cured at 55° C. for two hours.

Example 6

Polyurea Capsules Prepared with Diethylenetriamine

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y., USA), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 40% diethylenetriamine (Sigma-Aldrich, St. Louis, Mo.) was added under constant mixing with an overhead mixer. Formation of capsules was immediately visible by optical microscopy. The mixer speed was reduced after the addition of diethylenetriamine was complete. The capsule slurry was cured at 55° C. for two hours.

Example 7

Polyurea Capsules Prepared with Triethylenetetramine

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 70% triethylenetetramine (Sigma-Aldrich, St. Louis, Mo.) was added under constant mixing with an overhead mixer. Formation of capsules was immediately visible by optical microscopy. The mixer speed was reduced after the addition of triethylenetetramine was complete. The capsule slurry was cured at 55° C. for two hours.

Example 8

Polyurea Capsules Prepared with Tetraethylenepentamine

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 70% tetraethylenepentamine (Sigma-Aldrich, St. Louis, Mo.) was added under constant mixing with an overhead mixer. Formation of capsules was immediately visible by optical microscopy. The mixer speed was reduced after the addition of tetraethylenepetamine was complete. The capsule slurry was cured at 55° C. for two hours.

Example 9

Polyurea Capsules Prepared with Pentaethylenehexamine

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 70% pentaethylenehexamine (Sigma-Aldrich, St. Louis, Mo.) was added under constant mixing with an overhead mixer. Formation of capsules was immediately visible by optical microscopy. The mixer speed was reduced after the addition of pentaethylenehexamine was complete. The capsule slurry was cured at 55° C. for two hours.

Example 10

Polyurea Capsules Prepared with Branched Polyethyleneimide

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and 10.4 g of 49% branched polyethyleneimide (Sigma-Aldrich, St. Louis, Mo.) was added under constant mixing with an overhead mixer. Formation of capsules was immediately visible by optical microscopy. The mixer speed was reduced after the addition of branched polyethyleneimide was complete. The capsule slurry was cured at 55° C. for two hours.

Example 11

Polyurea Capsules Prepared with Nisin

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and a mixture containing 20.1 g of 60% Nisin (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of Nisin was complete. The capsule slurry was cured at 75° C. for two hours.

Example 12

Polyurea Capsules Prepared with 1,3-Diaminoguanidine Monohydrochloride

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and a mixture containing 10.1 g of 48% 1,3-diaminoguanidine monohydrochloride (Sigma-Aldrich, St. Louis, Mo.), 10 g of 50% sodium carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of 1,3-diaminoguanidine monohydrochloride was complete. The capsule slurry was cured at 75° C. for two hours.

Example 13

Polyurea Capsules Prepared with 1,1-Dimethylbiguanide Hydrochloride

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and a mixture containing 10.1 g of 46% 1,1-dimethylbiguanide hydrochloride (Santa Cruz Biotechnoloy, Dallas, Tex.), 10 g of 50% sodium carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of 1,1-dimethylbiguanide hydrochloride was complete. The capsule slurry was cured at 75° C. for two hours.

Example 14

Polyurea Capsules Prepared with Guanidine Carbonate

Preparation of the Fragrance Emulsion.

Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals corporation, Rye Brook, N.Y.), to form the oil phase. In a separate beaker, a solution (130 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules.

The fragrance emulsion was heated to 35° C. in a round bottom vessel and a mixture containing 10.1 g of 36% guanidine carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of guanidine carbonate was complete. The capsule slurry was cured at 75° C. for two hours.

Example 15

Physical Characterization of Polyurea Capsules

Figure 1A:
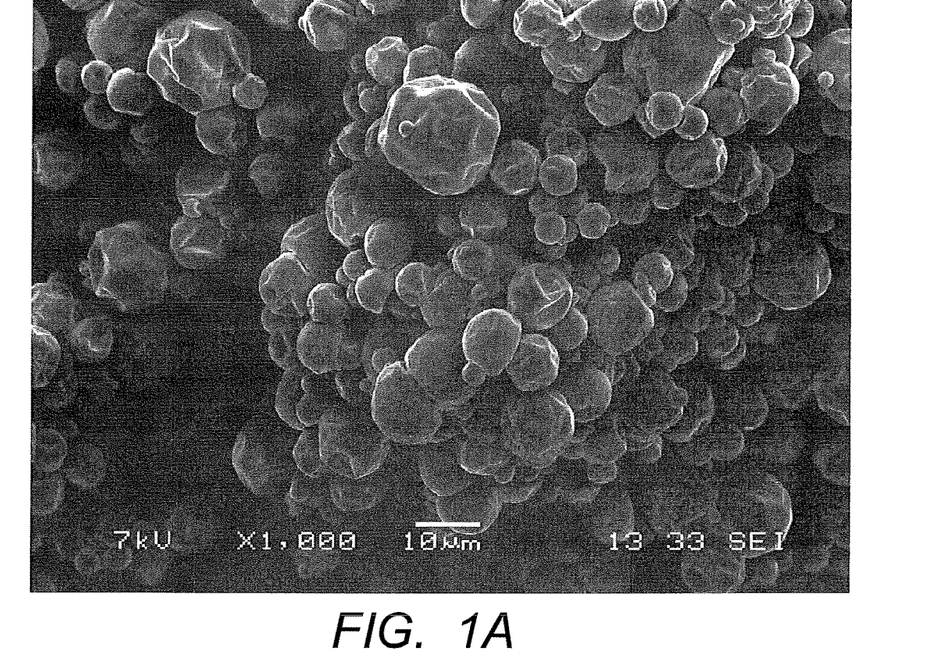
FIG. 1A shows a scanning electron microscope (SEM) image of capsules prepared in accordance with the present invention.
Figure 1B:
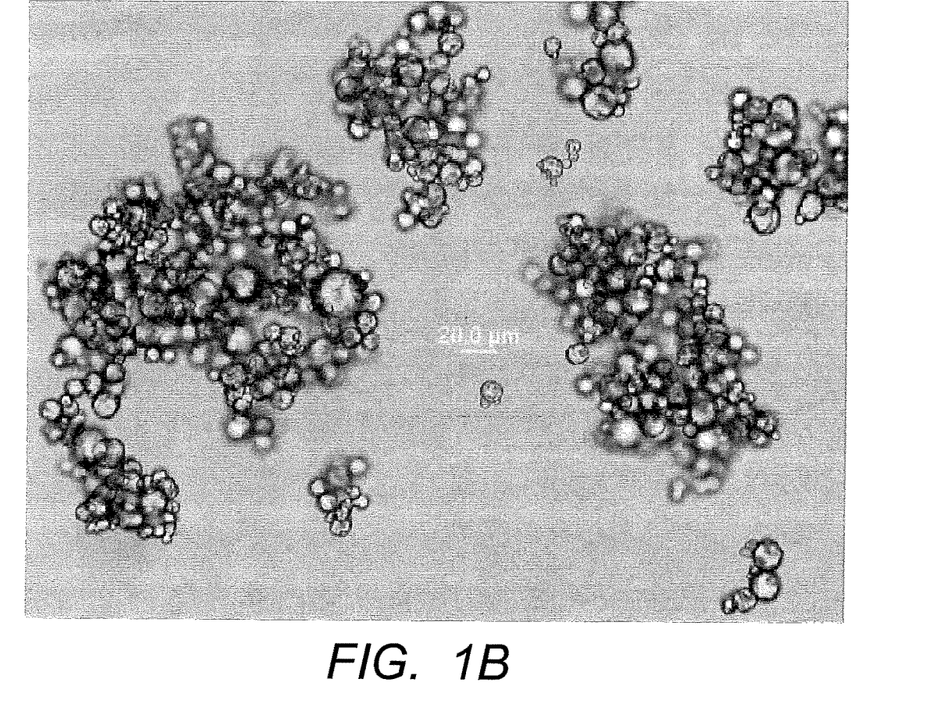
FIG. 1B shows an optical image of capsules prepared in accordance with the present invention.

The capsules prepared in Example 5 were analyzed with scanning electron microscopy (FIG. 1A) and optical microscopy (FIG. 1B). It was found that the capsules prepared in accordance with the present invention have robust mechanical stability.

Example 16

Fragrance Leakage from Polyurea Capsules

The capsule slurries prepared in Examples 3-15 were analyzed for fragrance leakage. The fragrance capsule slurries were diluted with DOWNY fabric softener (Procter & Gamble, Cincinnati, Ohio) to yield mixtures containing 0.5% capsule slurry. The mixtures were aged in an oven for 0, 3 and 6 days at 50° C. Three samples were prepared by filtering the mixtures through 1 µm filters (Fisher Scientific, Pittsburgh, Pa.). The content of free fragrance in the mixtures was analyzed. The results are presented in Table 1.

TABLE 1

| Sample | FO (%) | Percent Leakage | | |
|---|---|---|---|---|
| | | 0 days | 3 days @ 50° C. | 6 days @ 50° C. |
| Example 3 | 2.2 | <10 | 1 | 11 |
| Example 5 | 0.3 | <10 | <10 | <10 |
| Example 6 | 0.4 | <10 | 22 | 29 |
| Example 7 | 0.4 | 15 | 21 | 13 |
| Example 8 | 0.5 | <10 | <10 | 16 |
| Example 9 | 0.9 | <10 | <10 | 13 |
| Example 10 | 0.05 | <10 | <10 | <10 |
| Example 11 | 0.8 | <10 | <10 | <10 |
| Example 12 | 0.4 | <10 | <10 | <10 |
| Example 13 | 0.6 | <10 | <10 | <10 |
| Example 14 | 0.3 | <10 | <10 | <10 |

The results demonstrated that the capsules prepared in accordance with the present method had excellent stability.

Example 17

Perfumery Performance of Polyurea Capsules in a Hair Refresher Application

To establish the consumer benefits of the capsules of this invention, the capsule slurry prepared in Example 3 was blended into a hair refresher base and evaluated for its consumer benefits. The fragrance load was 0.25% neat equivalent. For comparison, a similar solution was prepared using neat fragrance at 0.5%. Hair swatches were sprayed with the dispersion and were air-dried overnight before being evaluated by a panel of 12 judges. The fragrance intensity was rated from a scale ranging from 0 to 10. A numerical value of 5 indicated the hair swatches produced a strong intensity, while a value of 10 indicated the hair swatches generated a very strong smell. The results of this analysis are presented in Table 2.

TABLE 2

| Samples | Pre-rubbing intensity | $I_{pre, capsule}/I_{pre, neat}$ | Post-rubbing intensity | $I_{post, capsule}/I_{post, neat}$ |
|---|---|---|---|---|
| Neat | 1.0 | | 1.2 | |
| Sample containing capsule after 24 hours | 2.5 | 2.5 | 6.3 | 5.25 |

The data demonstrated that the samples containing capsules prepared in accordance with this invention gave much stronger perfumery intensity at both the pre-rubbing and post-rubbing stage. The fragrance intensity of the samples containing capsules was 2.5 times that of the neat samples at the pre-rubbing stage and 5.25 that of the neat sample in the post-rubbing stage. This analysis indicated that the polyurea capsule provided significant and long-lasting perfumery benefits and suitable for a personal care application.

Example 18

Perfumery Performance of Polyurea Capsules in a Fabric Refresher Application

To establish the consumer benefits of the capsules of this invention, the capsule slurry prepared in Example 3 was blended into a fabric refresher base and evaluated for its consumer benefits. The fragrance load was 0.2% neat equivalent. For comparison, a similar solution was prepared using neat fragrance at 0.2%. Hair swatches were sprayed with the dispersion and air-dried for 72 hours before being evaluated by a panel of 6 judges. The fragrance intensity was rated on a scale ranging from 0 to 10. A numerical value of 5 indicated the hair swatches produced a strong intensity, while a value of 10 indicated the hair swatches generated a very strong smell. The results of the analysis are presented in Table 3.

TABLE 3

| Samples | Pre-rubbing intensity | $I_{pre, capsule}/I_{pre, neat}$ | Post-rubbing intensity | $I_{post, capsule}/I_{post, neat}$ |
|---|---|---|---|---|
| Neat | 1.0 | | 1.0 | |
| Sample containing capsule after 24 hours | 2.0 | 2.0 | 5.5 | 5.50 |

The results demonstrated that the samples containing capsules prepared in accordance with this invention gave much stronger perfumery intensity at both the pre-rubbing and post-rubbing stage. The fragrance intensity of the samples containing capsules was 2.0 times that of the neat samples at the pre-rubbing stage and 5.5 times that of the neat sample in the post-rubbing stage. This analysis indicated that the polyurea capsule provided significant and long-lasting perfumery benefits and suitable for fabric care application.

Example 19

Application Benefit of Polyurea Capsule in Hair Conditioner Application

Application benefit of the instant capsules in a personal care product was evaluated using a hair conditioner formulation. To conduct the experiment, the capsule slurry was dispersed in a hair conditioner base at 0.5% neat fragrance equivalent. The hair conditioner base was a Magick Botanicals oil-free conditioner base. To the base was added 1.0 g polyurea capsules. The formulation was applied to bundles of hair (40 g each), which contained four hair strands. The bundles were subsequently washed by wetting two bundles (8 strands) under water (water temperature: 100 F/38 C; flow rate: 1 gallon/minute) and lightly squeezing off the excess water. The hair was placed onto a balance and 2 g of unfragranced shampoo was directly applied onto the wet hair. The hair was lathered between palms, 10× clockwise and 10× counterclockwise, keeping the wax part of the swatches between two fingers (not to spread wax over surface of hair). The hair swatches were allowed to stand for 15 seconds and subsequently rinsed under a stream of water for 45 seconds. The process was repeated with hair conditioner. Excess water was gently squeezed out and the hair was allowed to dry overnight.

Figure 2:
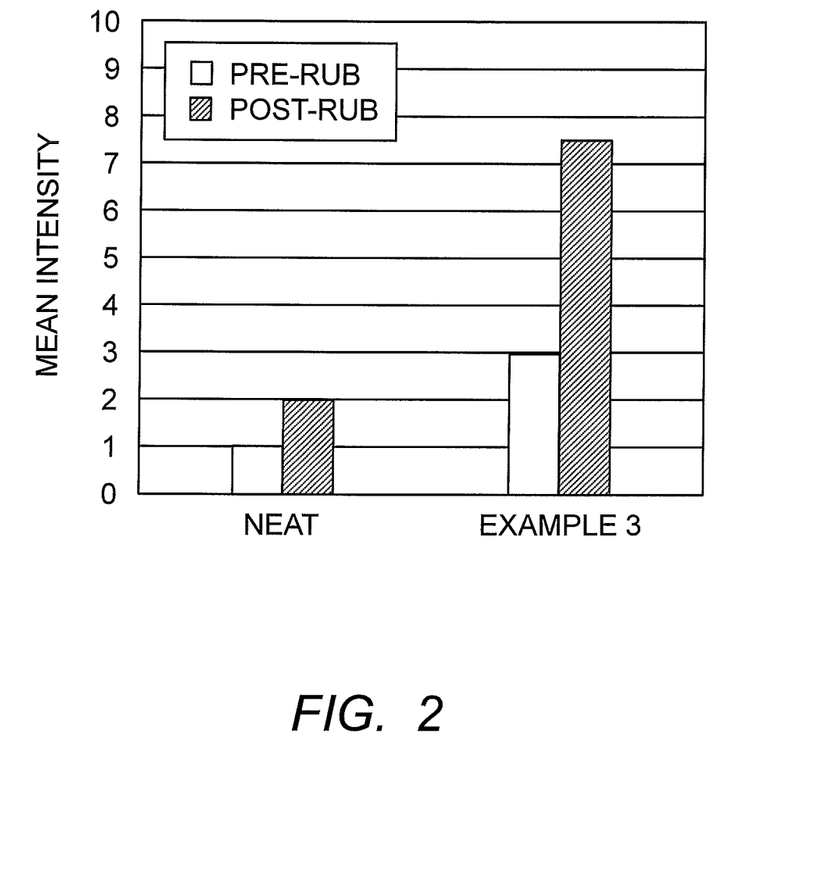
FIG. 2 shows the sensory performance of polyurea capsules of the invention in a hair conditioner formulation.

The dried samples were than evaluated by 16 trained panelists and the results are presented in FIG. 2. The results clearly demonstrate that the product containing polyurea capsules had much stronger perfumery intensity than the neat fragrance. Thus, the polyurea capsules of this invention can deliver excellent consumer benefits both in the pre- and post-rubbing stage.

What is claimed is:

1. A method for preparing a polyurea capsule composition comprising:
   (a) preparing an oil phase comprising an active material and a polyisocyanate;
   (b) preparing a surfactant solution;
   (c) emulsifying the oil phase into the surfactant solution to form a fragrance emulsion;
   (d) adding a cross-linking agent to the fragrance emulsion to form a capsule slurry;
   (e) curing the capsule slurry;
   (f) adding a salt to the cured capsule slurry; and
   (g) washing the capsule slurry with water,
   wherein the active material is a fragrance oil present at a level of about 5% to about 80% of the capsule composition; the polyisocyanate, added at a level of about 0.1% to about 10% by weight of the capsule composition, consists of a trimethylol propane-adduct of xylylene diisocyanate; the surfactant is added at a level of about 0.1% to about 5% by weight of the capsule composition; the cross-linking agent, added at a level of about 0.1% to about 5% by weight of capsule composition, is N,N'-bis(3-aminopropyl)-1,3-propanediamine, chitosan, nisin, or a combination thereof; an encapsulating polymer is formed by the polymerization reaction between the polyisocyanate and the cross-linking agent; and the encapsulating polymer encapsulates the active material.

* * * * *